United States Patent [19]

Pettit et al.

[11] Patent Number: 5,138,036

[45] Date of Patent: Aug. 11, 1992

[54] ISOLATION AND STRUCTURAL ELUCIDATION OF THE CYTOSTATIC CYCLODEPSIPEPTIDE DOLASTATIN 14

[75] Inventors: George R. Pettit, Paradise Valley, Ariz.; Yoshiaki Kamano, Tokyo, Japan; Cherry L. Herald, Tempe, Ariz.

[73] Assignee: Arizona Board of Regents acting on behalf of Arizona State University, Tempe, Ariz.

[21] Appl. No.: 435,622

[22] Filed: Nov. 13, 1989

[51] Int. Cl.$^5$ .......................... C07K 7/54; C07K 11/02
[52] U.S. Cl. .................... 530/323; 530/317; 514/908; 930/270; 930/DIG. 536
[58] Field of Search ................. 530/317, 323; 514/11, 514/9, 21, 908

[56] References Cited

U.S. PATENT DOCUMENTS

| | | | |
|---|---|---|---|
| 4,414,205 | 11/1983 | Pettit | 514/21 |
| 4,486,414 | 12/1984 | Pettit | 514/21 |
| 4,816,444 | 3/1989 | Pettit et al. | 514/17 |
| 4,879,278 | 11/1989 | Pettit et al. | 514/21 |

OTHER PUBLICATIONS

Rudinger, Peptide Hormones, Parsons (Ed.), U. Park Press, Baltimore, pp. 1–6 (1976).
Suffness et al., J. Natural Products, vol. 45, pp. 1–14 (1982).

*Primary Examiner*—Christina Cahn
*Attorney, Agent, or Firm*—Richard R. Mybeck

[57] ABSTRACT

A new cytostatic depsipeptide, designated "dolastatin 14", was isolated from the Indian Ocean shell-less mollusk *Dolabella auricularia*. Dolastatin 14 inhibited growth of the PS leukemia with $ED_{50}$ 0.0018 µg/mL. Pharmaceutical preparations and therapeutic regimens utilizing Dolastatin 14, its synthetic counterpart and pharmaceutically active derivatives are disclosed. Dolastatin 14 has the structural formula:

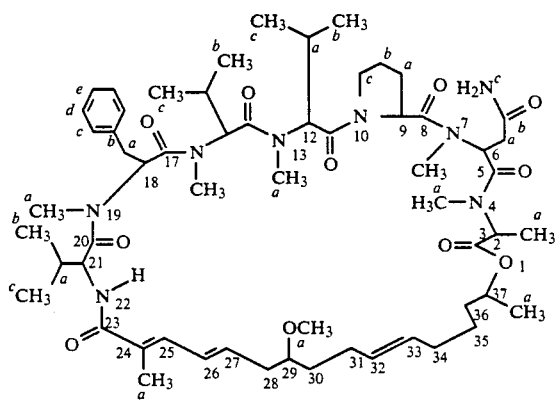

2 Claims, No Drawings

ISOLATION AND STRUCTURAL ELUCIDATION OF THE CYTOSTATIC CYCLODEPSIPEPTIDE DOLASTATIN 14

Financial assistance was provided by the National Cancer Institute PHS Grant CA-146049-05-12, DHHS Contract N01-CM-97262, NSF Grants CHE-8409644 and CHE-8620177 and numerous private foundations.

INTRODUCTION

The present invention relates to a cytostatic cyclodepsipeptide herein denominated "Dolastatin 14" which is obtained from the Indian Ocean shell-less mollusk *Dolabella auricularia:* to pharmaceutical preparations containing Dolastatin 14 as an essential active ingredient, and to methods of using such preparations to inhibit cell growth in a host afflicted therewith.

BACKGROUND OF THE INVENTION

The great Roman natural scientist Gaius Plinius Secundus (Pliny the Elder) in his comprehensive study, circa 60 AD, first described a most potent Indian Ocean sea hare of the genus Dolabella. (The Romans first designated Mollusca of the family Aplysidae as sea hares because of the similarity between the ears of a hare and the auriculate tentacles of these gastropods). However a consideration of the potential of the Indian Ocean Dolabella with respect to modern medical problems is only of recent origin. (See U.S. Pat. Nos. 4,414,205, Nov. 8, 1983, Dolastatins 1-3; 4,486,414, Dec. 4, 1984, Dolastatins A and B; and 4,816,444, Mar. 28, 1989, Dolastatin 10).

The dolastatins may correspond to the potent *D. auricularia* constituents (See: 1969 Ph.D. dissertation of M. Watson. U. of Hawaii, "Some Aspects of the Pharmacology, Chemistry and Biology of the Midgut Gland Toxins of Some Hawaiian Sea Hares, especially *Dolabella auricularia* and *Aplysia pulmonica*", University Microfilms Inc., Ann Arbor, Mich.)

The biological properties exhibited by the *Dolabella auricularia* have been pursued for centuries but it was only in 1972 that this laboratory found Indian Ocean specimens of this captivating sea hare which yielded extracts that proved effective (over 100% increase in life span) against the U. S. National Cancer Institute's (NCI) murine P388 lymphocytic leukemia (PS system). Subsequently, the Cancer Research Institute at Arizona State University, Tempe, Arizona succeeded in isolating ten new (and powerful) cell growth inhibitory and-/or antineoplastic peptides which were designated dolastatins 1 through 10.

Of the early work, dolastatin 1 was found to be the most active (lowest dose) antineoplastic substance (33% cure rate against the NCI murine B16 melanoma at 11 $\mu$g/kg) known in its time. Because of the dolastatin's potency, the sea hare seems to require only vanishingly small quantities (about 1 mg each from 100 kg), making isolation and structural elucidation of these peptides exceptionally challenging. Later another substance was isolated and determined to be a unique linear pentapeptide and was demoninated "dolastatin 10". This substance was the most important *Dolabella auricularia* antineoplastic constituent located as it appeared to be the most active (lowest dose) antineoplastic substance found up to its time. In practice, dolastatin 10 showed a 17-67% curative response at 3.25-26 $\mu$g/kg against the National Cancer Institute ("NCI") human melanoma xenograph (nude mouse), 42-138 % life extension at 1.44-11.1 $\mu$g/kg using the B16 melanoma and 69-102% life extension at 1-4 $\mu$g/kg against the PS leukemia ($ED_{50}=4.6\times10^5$ $\mu$g/ml). In contrast, dolastatin 14 is strongly active against NCI's P388 lymphocytic leukemia (PS System) (See: Schmidt et al, *Experienta,* 1978, 37, 659-660) cell line with an $ED_{50}$ of 0.0018 $\mu$g/ml. The PS System is generally accepted as an excellent predictor of activity against various types of human cancer (See: Vendetti et al, *Lloydia,* 30, 332 et seq (1967) and references cited therein).

BRIEF SUMMARY OF THE INVENTION

The present invention relates to the discovery of a new and potent cytostatic substance demoninated "Dolastatin 14" which is extracted from the Indian Ocean shell-less mollusk *Dolabella auricularia* in the manner hereinafter described in detail. The substance, its synthetic counterpart and non-toxic pharmaceutically acceptable deriatives can be formulated into useful pharmaceutical preparations having demonstrable and confirmable levels of cell growth inhibitory activity when measured by the generally accepted protocols in use at the United States National Cancer Institute.

Accordingly, a principal object of the present invention is to provide a new agent useful in the retardation or remission of one or more types of malignant cells.

Another object of the present invention is to provide methods and procedures for isolating a cell growth inhibitory substance from marine life in a form in which it may be readily and usefully employed in the therapeutic treatment and management of one or more types of neoplasms which occur in human hosts.

A further object of the present invention is to provide means and methods of creating useful pharmaceutical preparations for the treatment and management of neoplastic disease which preparations contain as their essential active ingredient a unique cytostatic factor obtained from the Indian Ocean shell-less mollusk *Dolabella auricularia,* its synthetic counterpart, or a nontoxic pharmaceutically active derivative thereof.

These and still further objects as shall hereinafter appear are readily fulfilled by the present invention in a remarkably unexpected manner as will be readily discerned from the following detailed description of an exemplary embodiment thereof.

DETAILED DESCRIPTION OF THE INVENTION

The Organism

Taxonomy: *Dolabella auricularia* belongs to the family Aplysidae, the class Gastropoda and the phylum Mollusca. In a reference by H. Engel in "Zoologische Mededeelingen,"Leiden, 24, 197-239 (1945), there are numerous color plates of specimens of Dolabella. Also in this reference is a listing of previously presumed different species of Dolabella which were later found to be the same and identified as *Dolabella auricularia.* These species are: *Dolabella agassizi, D. andersonii, D. hasseltii, D. hemprichii, D. neira, D. peronii, D. rumphii, D. teremidi, D. tongana, D. truncata, D. variegata,* and *D. scapula.*

In appearance, the Dolabella used herein were olive green in color having a pear-shaped body and average length, 15-20 cm. The reference by H. Engel has detailed descriptions of Dolabella collected around the world.

The Dolabella collection site used for initial isolation of the dolastatins was on the eastern side of Mauritius in the Indian Ocean, approximate location, 21 S latitude, 56 E longitude, in 4-5 ft. deep water off the coast of the island.

Another site where Dolabella can be collected is near Negros Island in the Philippines, approximate location 9 N latitude, 123 E longitude. Extracts of Dolabella species from five separate collections all contained antineoplastic activity.

Isolation and Purification of Dolastatin 14

A variety of methods can be used to isolate and purify the various dolastatins from samples of sea hare, such as, solvent extraction, partition chromatography, silica gel chromatography, (wet and dry system), preparative thin-layer chromatography and crystallization from solvents.

Isolation of Dolastatin 14

A combined ethanol-2-propanol extract of *D. auricularia* (1,000 kg. wet, collected in 1982) was concentrated to an active methylene chloride fraction by a series of solvent partition steps. Extensive column chromatographic separation (steric exclusion and partition on SEPHADEX, partition and absorption on silica gel and HPLC) using gradient elution techniques guided by PS bioassay led to 12.0 mg of pure dolastatin 14, ($1.2 \times 10^{-7}$% yield, from 1000 kg of wet sea hare). Final purification by HPLC on PARTISIL-10 ODS-2 (gradient elution with 1:1 to 9:1 methanol-water) and precipitation from methanol afforded a pure specimen of dolastatin 14 as an amorphous powder: (12.0 mg total, $1.2 \times 10^{-7}$% yield) from methanol: mp 123°-125° C.; $[\alpha]_D^{24} -146°$ (c=0.14), MeOH; tlc ($R_f$ 0.35 in 90:10:0.8 $CH_2Cl_2$:MeOH:$H_2O$); UV ($CH_3OH$) $\lambda$max 211 ($\epsilon$23,420) and $\lambda$max 262 ($\epsilon$14,160) nm; IR (NaCl plate), $\nu$max 3320, 2963, 2930, 2875, 1732, 1670, 1640, 1510, 1455, 1405, 1360, 1315, 1100, 785 and 700 cm$^{-1}$; high resolution SP-SIMS, 1089.7009 (M+H)$^+$, $C_{59}H_{93}N_8O_{11}$ requires 1089.6964, FAB MS [M+H] 1089.6964. Amino acid analyses suggested the presence of valine and proline.

In contrast to our prior experience with utilizing collision activated decomposition (MS/MS) of HREI ions from dolastatin-type peptides to assist in structural elucidation the mass spectral fragmentation of dolastatin 14 (1) gave primarily abstruse results. However, an unequivocal structure (1) for dolastatin 14 was eventually deduced by combining various high field (400 MHz) NMR techniques that included $^1H,^1H$-COSY (see: Table 1, infra) and $^1H$, $^1H$-relayed COSY. By means of these methods the new hydroxy hexadecenoic acid (herein named dolatrienoic acid) and amino acid units were ascertained. Two of the olefin segments of dolatrienoic acid were clearly E as the respective vinyl protons were coupled with J = ~15 Hz. The E configuration for the trisubstituted double bond was derived from the very large $^1H$-[$^1H$]-NOE difference experiment value involving the C-24a methyl proton and the proton at C-26.

The sequence of dolastatin 14 components was established primarily by results of COSY, HETCOR, NOE and heteronuclear multiple bond correlation (HMBC) NMR experiments in methylene chloride-$d_2$. The most difficult connectivity problems were solved as follows. Lack of an N-10 to C-11 connection in the HMBC spectra was circumvented by the strong NOE's observed in both directions between the protons at C-9c and C-12. In methylene chloride-$d_2$ the carbonyl group chemical shifts of C-23 and C-5 fell within 0.1 ppm of one another and did not allow an unambiguous linkage assignment in the ring system. However in acetone-$d_6$ the difference increased to 0.3 ppm and their connections were then safely established using HMBC methods. When the C-6a proton absorbing at 2.99$\delta$ was irradiated, strong NOE's were observed for both of the amide protons at N-6c thereby locating this otherwise elusive amino group.

Based on our complete structure determinations for dolastatins 3, 10 and 15 it appears likely that the Phe, Pro and Val amino acid units of dolastatin 14 bear the usual S-configuration. Conclusive evidence for these assumptions and chiral assignments for the N-Me-Ala, N-Me-Asn and dolatrienoic acid units will have to await larger scale reisolation and/or synthesis of dolastatin 14.

Drawing on the complete structure determination for dolastatins 3, 10 and 15, it was determined that the Phe, Pro and Val amino acid units of dolastatin 14 bear the usual S-configuration and that dolastatin 14 has the following structure:

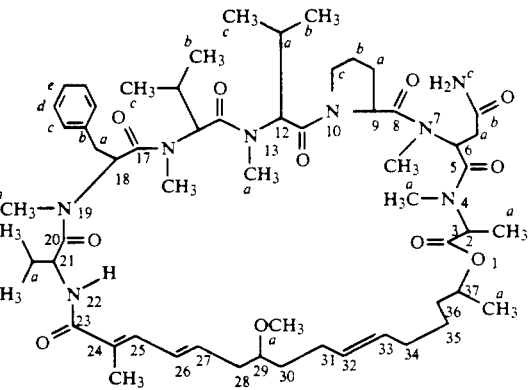

TABLE I

| Dolastatin 14 Correlated $^{13}$C and $^1$H NMR Assignments in Dichloromethane-$d_2$ Solution$^a$ | | |
|---|---|---|
| Structure Assignment | $^{13}$C | Chemical Shift, ppm $^1$H Mult, J (Hz) |
| 2 | 171.0 | |
| 3 | 55.8 | 4.82 q (7.0) |
| 3a | 16.1 | 1.45 d (7.0) |
| 4a | 29.9 | 2.75 s |
| 5 | 169.4 | |
| 6 | 49.7 | 5.77 dd (9.3, 5.3) |
| 6a | 35.5 | 2.37 dd (15.3, 5.3) |
| | | 2.99 dd (15.3, 9.3) |
| 6b | 172.1 | |
| 6c | | 5.25 brs, 5.75$^b$ |
| 7a | 30.5 | 2.93 s |
| 8 | 171.6 | |
| 9 | 57.6 | 4.66 dd (8.8, 4.0) |
| 9a | 28.7 | 1.67 m, 2.02 m |
| 9b | 25.1 | 1.67 m, 1.87 m |
| 9c | 47.7 | 3.52 m, 3.68 m |
| 11 | 168.6 | |
| 12 | 60.1 | 4.89 d (10.8) |
| 12a | 27.2 | 2.08 d heptet (10.8, 6.7) |
| 12b | 18.1 | 0.50 d (6.8) |
| 12c | 19.8 | 0.88 d (6.5) |
| 13 | 30.4 | 2.64 s |
| 14 | 170.3 | |
| 15 | 58.9 | 5.01 d (10.7) |
| 15a | 27.9 | 2.15 d heptet |

TABLE I-continued
Dolastatin 14 Correlated $^{13}$C and $^{1}$H NMR
Assignments in Dichloromethane-$d_2$ Solution[a]

| Structure Assignment | $^{13}$C | Chemical Shift, ppm $^{1}$H Mult, J (Hz) |
|---|---|---|
| | | (10.7, 6.7) |
| 15b | 18.5 | 0.72 d (6.8) |
| 15c | 19.7 | 0.78 d (6.5) |
| 16a | 29.9 | 2.67 s |
| 17 | 169.6 | |
| 18 | 55.0 | 5.74 dd (8.4, 7.0) |
| 18a | 35.6 | 2.83 dd (13.7, 7.0) |
| | | 3.25 dd (13.7, 8.4) |
| 18b | 137.7 | |
| 18c | 129.9 × 2 | 7.22 m |
| 18d | 128.6 × 2 | 7.21 m |
| 18e | 126.9 | 7.19 m |
| 19a | 31.1 | 3.11 s |
| 20 | 172.9 | |
| 21 | 55.2 | 4.65 t (9.9) |
| 21a | 30.8 | 1.95 heptet (9.9, 6.6) |
| 21b | 18.6 | 0.64 d (6.5) |
| 21c | 19.1 | 0.90 d (6.7) |
| 22 | | 6.01 d (9.9) |
| 23 | 169.3 | |
| 24 | 128.4 | |
| 24a | 12.9 | 1.88 (2.2) |
| 25 | 134.7 | 6.70 dq (11.2, 2.2) |
| 26 | 127.8 | 6.35 dd (14.9, 11.2) |
| 27 | 138.0 | 5.99 dd (14.9, 8.8, 6.1) |
| 28 | 37.1 | 2.30 m, 2.48 m |
| 29 | 80.0 | 3.27 m |
| 29a | 56.9 | 3.32 s |
| 30 | 34.4 | 1.47 m |
| 31 | 33.08 | 2.02 |
| 32 | 131.2 | 5.44 dt (15.1, 6.1) |
| 33 | 130.8 | 5.38 dt (15.1, 6.1) |
| 34 | 33.1 | 2.02 m |
| 35 | 26.6 | 1.30 m |
| 36 | 35.6 | 1.37 m, 1.63 m |
| 37 | 73.1 | 4.79 m |
| 37a | 19.8 | 1.20 d (6.1) |

[a]Residual CHDCl$_2$ as internal reference ($\delta$ 5.32)
[b]Overlapping signal To further assist in the understanding of the present invention, a more detailed description of the experimental procedures now follows.

General Methods Solvents used for chromatographic procedures were redistilled. The SEPHADEX®LH-20 (25–100 $\mu$) employed for gel permeation and partition chromatography was obtained from Pharmacia Fine Chemicals AB, Uppsala, Sweden. Gilson FC-220 race track and FC-80 micro-fractionators connected to Gilson HM UV-VISIBLE HOLOCHROME detectors were used for chromatographic fractionation experiments. Column chromatographic procedures with silica gel utilized the 70–230 mesh or SILICA GEL 60 prepacked columns supplied by E. Merck (Darmstadt). A PARTISIL M9 10/50 ODS-2 (C-18 reverse phase) column (9.4 mm i.d. × 500 mm) was used for HPLC and obtained from Whatman, Inc. Clifton, N.J. Preparative layer plates were also obtained from Whatman, Inc. and the SILICA GEL GF Uniplates for TLC were supplied by Analtech, Inc., Newark, Del. The TLC plates were viewed with UV light, developed with an anisaldehyde-acetic acid-sulfuric acid spray (heating at approx. 150° C. for 10 min) or with ceric sulfate-sulfuric acid (heating for 10 min).

Amino acid analyses were performed with a Beckman Model 121 unit. Ultraviolet spectra were recorded using a HEWLETT-PACKARD 8450A UV/VIS spectrophotometer equipped with a HP7225A plotter. The infrared spectra were recorded with a NICOLET MX-1 FT instrument. High resolution SP-SIMS mass spectra were obtained using V.G. Analytical MM ZAB-2F and KRATOS MS-50 triple analyzer mass spectrometers. High resolution electron impact mass spectra (m/$\Delta$m ~ 10,000) were recorded on KRATOS MS-80 and MS-50 instruments. The NMR experiments (in various solvents using a BRUKER 5-mm $^{1}$H $^{13}$C dual switchable probehead) were conducted using a BRUKER AM-400 narrow bore spectrometer with an ASPECT 3000 computer and pulse programmer operating at 400.13 and 100.62 MHz for $^{1}$H-and $^{13}$C-NMR, respectively.

Animal Collection, Extraction, and Preliminary Experiments. The Western Indian Ocean (Mauritius) sea hare *Dolabella auricularia* was initially collected in October 1972. By March 1975 confirmed activity of an ethanol extract against the National Cancer Institute's (NCI) P388 lymphocytic leukemia (PS system) was established and showed T/C 235 at 600 mg to 167 at 176 mg/kg. A series of analogous extracts from subsequent recollections of the sea hare gave comparable results. The experiments reported herein were conducted with a 1982 recollection (same site) preserved in ethanol. The total volume of animal (~ 1,000 kg) and ethanol preservative was 700 gallons.

After extraction and solvent partitioning 2.75 kg of methylene chloride concentrate was obtained for large-scale preparative HPLC. Two columns in series (6" × 10') were packed with silica gel (DAVISIL 633, 200–400 mesh, slurry packed in 7:3 hexane-ethyl acetate). The 2.75 kg of dark (green-black) concentrate was dissolved in ethyl acetate (2 gal) and pumped onto the column and chromatogaphed using the following solvent gradients at a rate of 60–72 l/h.

| Eluant | Eluant Vol. (l) | Fraction No. | Fraction Residue (g) |
|---|---|---|---|
| 70/30 hexane:ethyl acetate | 200 | 1 | 64.9 |
| 60/40 hexane:ethyl acetate | 120 | 2–8 | 282 |
| 50/50 hexane:ethyl acetate | 240 | 8–9 | 78 |
| | | 10–14 | 160.1 |
| | | 15–16 | 58 |
| | | 17–18 | 72.2 |
| 100% ethyl acetate | 120 | 19–21 | 74.9 |
| | | 22–25 | 70.6 |
| 95:5:0.7 ethyl acetate methanol-water | 120 | 26–28 | 156.4 |
| | | 29–31 | 50.5 |
| 83:17:1.4 ethyl acetate-methanol-water | 240 | 32–35 | 42.7 |
| | | 36–38 | 50.3 |
| | | 39 | 66.2 |
| | | 40 | 76 |
| | | 41–45 (A) | 132 |
| 67:33:2.5 ethyl acetate-methanol-water | 240 | 46–50 (B) | 72 |
| | | 51 | 77 |
| | | 52–55 | 209.5 |
| 50:50:5 ethyl acetate-methanol-water | | 56–60 | 56 |
| 45:45:10 ethyl acetate-methanol-water | | 61–65 | 100 |
| | | 66–69 | 30.5 |

Each fraction was eluted with 20 l of solvent and comparable (by TLC) fractions were combined. Isolation of Dolastatin 14. From the preparative HPLC fractions, two displayed significant activity in the P388 system, fraction A (132.0 g PS T/C toxic 165 at 30→7.5 mg/kg and ED$_{50}$ < 10$^{-2}$) and fraction B (72.0 g, PS T/C toxic 141 at 35→8.7 mg/kg and $ED_{50} < 10^{-2}$). The fractions were combined and dried to give 190.4 g. An aliquot (38 g) was treated as shown below in the Separation Schemes, Part 1, Part 2, Part 3, Part 4, Part 5, and Part 6.

A variety of methods can be used to isolate and purify the various dolastatins from samples of sea hare, such as, solvent extraction, partition chromatography, silica gel chromatography (wet and dry system), preparative thin-layer chromatography and crystallization from solvents.

In a typical series of experiments, the 38 g of fraction A+B was chromatographed on a column of SEPHADEX LH-20 (10×120 cm) in 1:1 methylene chloride-methanol. Combination of similar fractions gave fractions C-J as outlined in Separation Scheme Part 1, supra. The active (in vivo) fractions D and E were combined and divided into two equal parts (6.0 each) for separation using silica gel column chromatography. The I-1 series was further separated by dry column chromatography with a gradient of 990:10:0.1 to 100:100:1 ethyl acetate-methanol- water to give active fractions K, L, and M. The parallel I-2 series was also separated by dry column chromatography using methylene chloride-methanol and the gradient 99:1 to 1:1 giving active fraction N. Combined fractions K, L, M (2.6 g) were separated using dry column silica gel chromatography and a 99:1 to 1:1 methylene chloride-methanol gradient to give active fractions O-S (1.15 g) as detailed on Separation Scheme Part 2, supra. The combined active fractions O-S were then separated again on a column of silica gel, using a 99:1 to 4:1 methylene chloride-methanol gradient that resulted in 10 fractions (f1→f10).

The fraction f8 (247.6 mg) was chromatographed on silica gel column with ethyl acetate-methanol-water (99:1:1:0.1 4:1:0.1) to give the fraction f8-4 (23.9 mg) as outlined on Separation Scheme Part 3. This fraction was separated with SEPHADEX LH-20 using 4:5:1 hexane-$CH_2Cl_2$—$CH_3OH$ as solvent. An active fraction f8-4-1 (3.3 mg) ($ED_{50} 5.7 \times 10^{-3}$), was combined with another active fraction f7-2 (1.2 mg) $ED_{50}$ $1.5 \times 10^{-1}$), which was obtained from the fraction 7 (19.5 mg) by the SEPHADEX LH-20 separation. Total fraction (4.5 mg) was separated by a three step procedure including preparative TLC separation as described in separation of dolastatin 10 (Part 2) to give 2.5 mg of dolastatin 14 ($ED_{50} 2.3 \times 10^{-2}$ and $1.9 \times 10^{-3}$). The SEPHADEX LH-20 separation of fraction N-2 (0.58 g) afforded two active fractions T (101.8 mg) and U (88.2 mg), respectively (See: Part 4). Active fractions T and U were combined (0.19 g) and further purified on columns of silica gel (wet with solvent) employing a 99:1 to 1:1 methylene chloride-methanol gradient. The resulting active fraction X (18.1 mg) was finally purified using HPLC (ODS-2 column) with a 1:1 to 9:1 methanol-water gradient. Another active fraction X-1 (36.1 mg) was also purified by SEPHADEX LH-20 procedure and HPLC (ODS-2 column) separation, as described in the case of dolastatin 10. Thus, series I-2 yielded 3.7 mg of pure dolastatin 14 (Part 4)

The larger amount of fraction A+B (152 g) was chromatographed on columns (10×120 cm) of SEPHADEX LH-20 in five portions in 1:1 methylene chloride-methanol as described in Separation Scheme Part 3, supra. The active fractions were combined and further separated using a column (4.5×80 cm; 1.2 kg) of silica gel and a stepwise gradient of methylene chloride-methanol (49:1 23:2, 9:1, 22:3, 17:3, 4:1, 1:1 and lastly, 100% methanol) to give active fraction b (6.87 g). Fraction b was rechromatographed on silica gel (dry) using a 99:1 to 1:1 methylene chloride-methanol gradient. The resulting active fractions d-i (4.6 g) were combined and chromatographed (dry column) on silica gel using a 99:1 to 1:1 ethyl acetate-methanol gradient to give active fractions j, k, k-1 and k-2. Two active fractions k-1 (715.3 mg; $ED_{50} 2.2 \times 10^{-3}$) and k-2 (413.5 mg; $ED_{50} 1.8 \times 10^{-3}$) in Separation Scheme Part 5, as shown in Part 6, were combined. The SEPHADEX LH-20 separation afforded an active fraction f4 (288.4 mg; $ED_{50} 1.4 \times 10^{-3}$), which was chromatographed on a silica gel column with 99:1→1:1 $CH_2Cl_2$—$CH_3OH$ as solvent to give an active fraction f9 (76.7 mg; $ED_{50}$ $1.8 \times 10^{-3}$) (crude dolastatin 14). The purification of crude dolastatin 14 on reverse phase HPLC column (ODS-2) with 1:1→9:1 $CH_3OH$—$H_2O$ gave pure (5.8 mg) dolastatin 14 ($ED_{50} 1.8 \times 10^{-3}$).

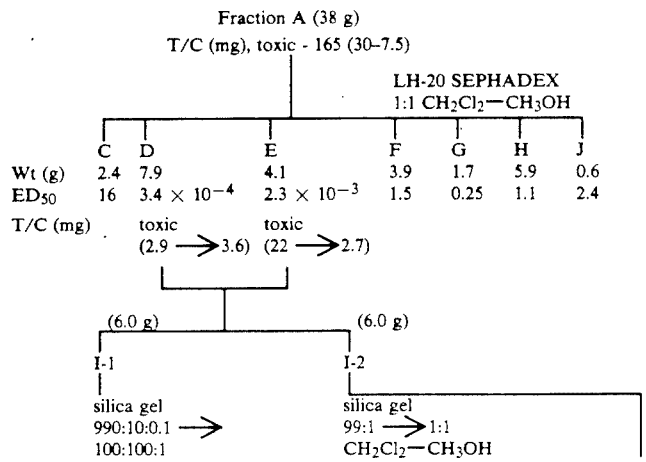

-continued
SEPARATION SCHEME
PART 1
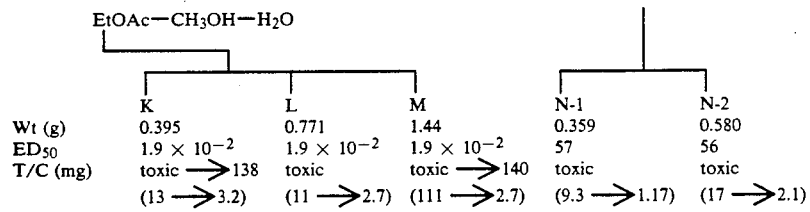
|          | K                  | L                  | M                  | N-1     | N-2     |
|----------|--------------------|--------------------|--------------------|---------|---------|
| Wt (g)   | 0.395              | 0.771              | 1.44               | 0.359   | 0.580   |
| ED$_{50}$ | $1.9 \times 10^{-2}$ | $1.9 \times 10^{-2}$ | $1.9 \times 10^{-2}$ | 57      | 56      |
| T/C (mg) | toxic →138         | toxic              | toxic →140         | toxic   | toxic   |
|          | (13 →3.2)          | (11 →2.7)          | (111 →2.7)         | (9.3 →1.17) | (17 →2.1) |
SEPARATION SCHEME
PART 2
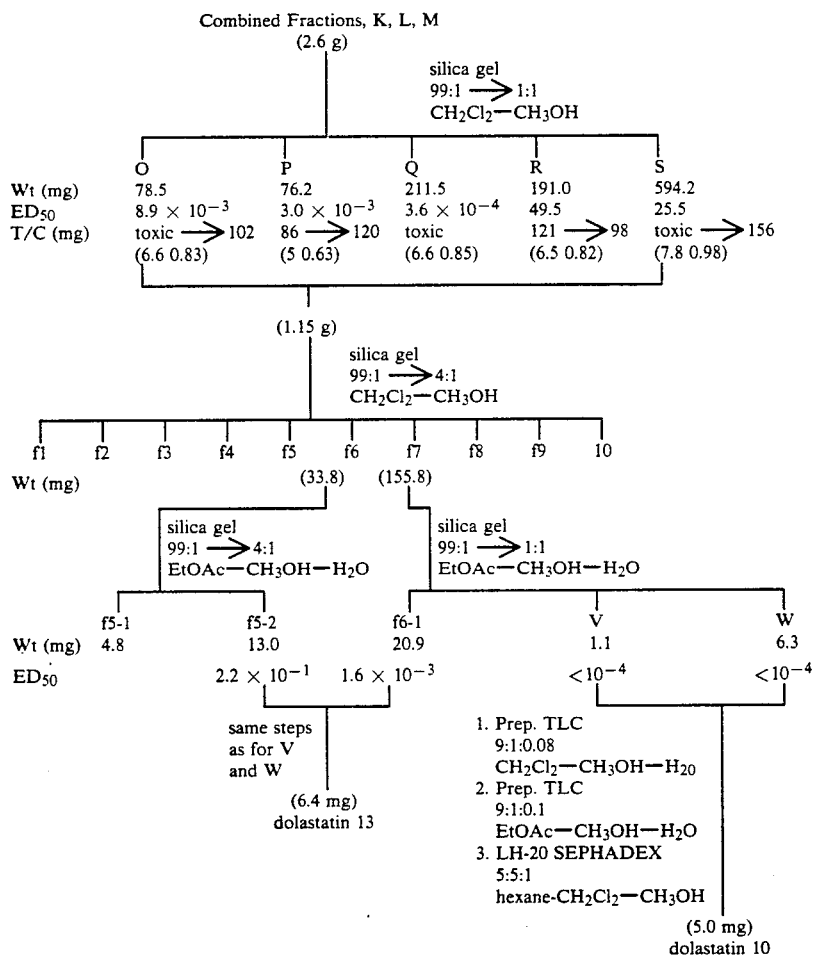
SEPARATION SCHEME
PART 3
(from Part 2)
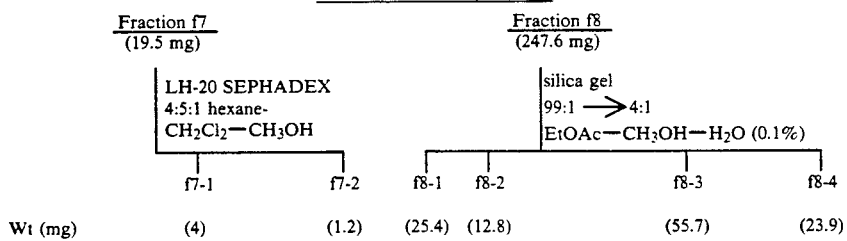

-continued
SEPARATION SCHEME
PART 3
(from Part 2)
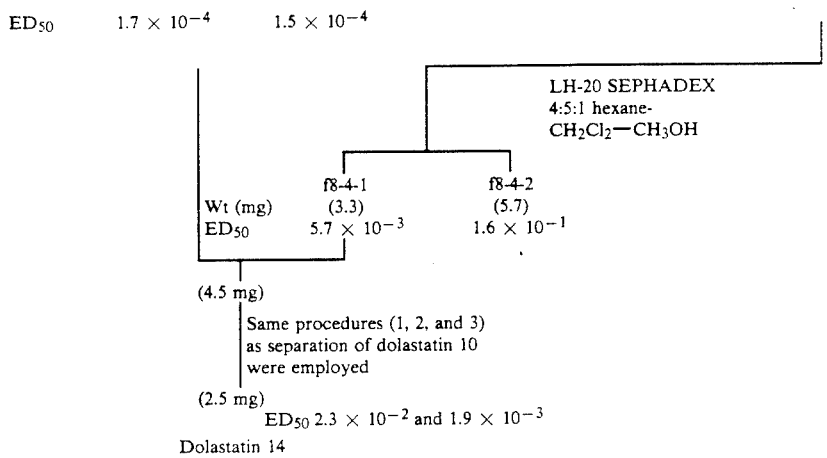
SEPARATION SCHEME
PART 4
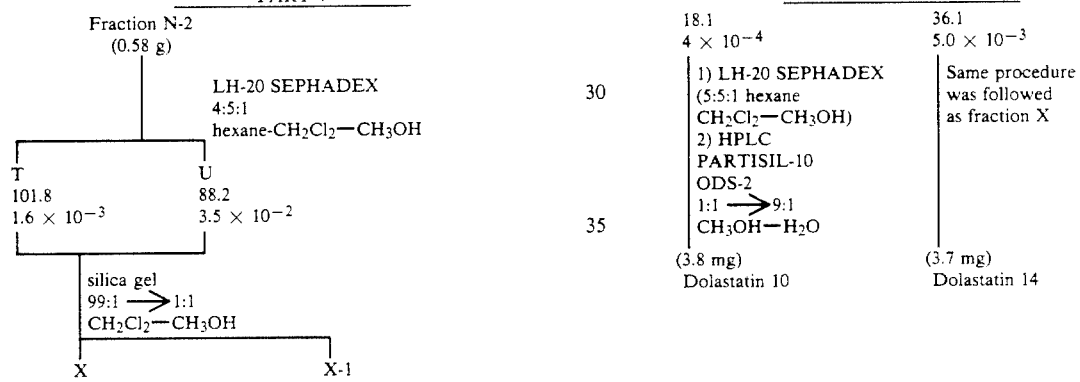
SEPARATION SCHEME
PART 5
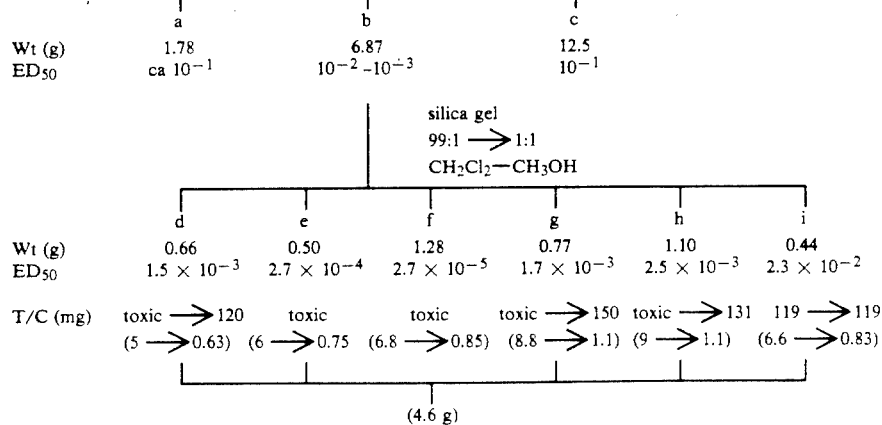

-continued
SEPARATION SCHEME
PART 5

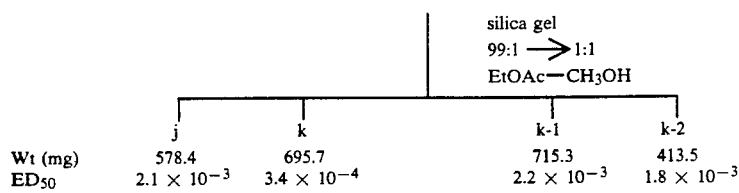

|  | j | k | k-1 | k-2 |
|---|---|---|---|---|
| Wt (mg) | 578.4 | 695.7 | 715.3 | 413.5 |
| $ED_{50}$ | $2.1 \times 10^{-3}$ | $3.4 \times 10^{-4}$ | $2.2 \times 10^{-3}$ | $1.8 \times 10^{-3}$ |

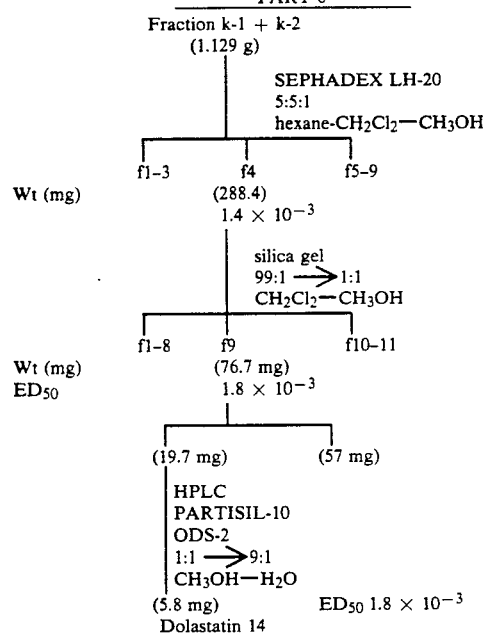

SEPARATION SCHEME PART 6

The administration of dolastatin 14 its synthetic counterpart, and its pharmaceutically active physiologically compatible derivatives is useful for treating animals or humans bearing a neoplastic disease which has recognized correlation with the NCI PS system such, for example, as acute myelocytic leukemia, acute lymphocytic leukemia, malignant melanoma, adenocarcinoma of lung, neuroblastoma, small cell carcinoma of lung, breast carcinoma, colon carcinoma, ovarian carcinoma, bladder carcinoma, and the like.

The dosage administered will be dependent upon the identity of the neoplastic disease; the type of host involved, including its age, health and weight; the kind of concurrent treatment, if any; the frequency of treatment and therapeutic ratio.

Illustratively, dosage levels of the administered active ingredients are: subcutaneously, one to about 50 mg/kg; intravenous, 0.to about 20 mg/kg; intramuscular, 1 to about 50 mg/kg; orally, 5 to about 100 mg/kg; intranasal instillation, 5 to about 100 mg/kg; ,and aerosol, 5 to about 100 mg/kg. As used herein, mg/kg means weight of active ingredient in milligrams divided by the body weight of the host in kilograms.

Expressed in terms of concentration, an active ingredient can be present in the compositions of the present invention for localized use about the cutis, intranasally, pharyngolaryngeally, bronchially, intravaginally, rectally, or ocularly in a concentration of from about 0.01 to about 50% w/w of the composition; and for parenteral use in a concentration of from about 0.05 to about 50% w/v of the composition and preferably from about 5 to about 20% w/v.

The composition of the present invention are preferably presented for administration to humans and animals in unit dosage forms, such as tablets, capsules, pills, powders, granules, suppositories, sterile parenteral solutions or suspensions, sterile non-parenteral solutions or suspensions, and oral solutions or suspensions and the like, containing suitable quantities of an active ingredient.

For oral administration either solid or fluid unit dosage forms can be prepared.

Powders are prepared quite simply by comminuting the active ingredient to a suitable fine size and mixing with a similarly comminuted diluent. The diluent can be an edible carbohydrate material such as lactose or starch. Advantageously, a sweetening agent or sugar is present as well as a flavoring oil.

Capsules are produced by preparing a powder mixture as hereinbefore described and filling the mixture into formed gelatin sheaths. As an adjuvant to the filling operation, a lubricant such as a talc, magnesium stearate, calcium stearate and the like can be added to the powder mixture before the filling operation.

Soft gelatin capsules are prepared by machine encapulation of a slurry of active ingredients with an acceptable vegetable oil, light liquid petrolatum or other inert oil or triglyceride.

Tablets are made by preparing a powder mixture, granulating or slugging, adding a lubricant and pressing into tablets. The powder mixture is prepared by mixing an active ingredient, suitable comminuted, with a diluent or base such as starch, lactose, kaolin, diacalcium phosphate and the like. The powder mixture can be granulated by wetting with a binder such as corn syrup, gelatin solution, methylcellulose solution or acacia mucilage and forcing through a screen. As an alternative to granulating, the powder mixture can be slugged, i.e., run through the tablet machine and the resulting imperfectly formed tablets broken into pieces (slugs). The slugs can be lubricated to prevent sticking to the tablet-forming dies by means of the addition of stearic acid, a stearic salt, talc or mineral oil. The lubricated mixture is then compressed into tablets.

When desired, each tablet can be provided with a protective coating consisting of a sealing coat or enteric coat of shellac, a coating of sugar and methylcellulose and a polish coating or carnauba wax.

Fluid unit dosage forms for oral administration such as syrups, elixirs and suspensions can be prepared wherein each teaspoonful of composition contains a predetermined amount of active ingredient for administration. The water-soluble forms can be dissolved in an aqueous vehicle together with sugar, flavoring agents and preservatives to form a syrup. An elixir is prepared by using a hydroalcoholic vehicle with suitable sweeteners together with a flavoring agent. Suspensions can be prepared of the insoluble forms with a suitable vehicle with the aid of a suspending agent such as acacia, tragacanth, methylcellulose and the like.

For parenteral administration, fluid unit dosage forms are prepared utilizing an active ingredient and a sterile vehicle, water being preferred. The active ingredient, depending on the form and concentration used, can be either suspended or dissolved in the vehicle. In preparing solutions the water-soluble active ingredient can be dissolved in water for injection and filter sterilized before filling into a suitable vial or ampule and sealing. Advantageously, adjuvants such as a local anesthetic, preservative and buffering agents can be dissolved in the vehicle. Parenteral suspensions are prepared in substantially the same manner except that an active ingredient is suspended in the vehicle instead of being dissolved and sterilization can not be accomplished by filtration. The active ingredient can be sterilized by exposure to ethylene oxide before suspending in the sterile vehicle. Advantageously, a surfactant or wetting agent is included in the composition to facilitate uniform distribution of the active ingredient.

In addition to oral and parenteral administration, the rectal and vaginal routes can be utilized. An active ingredient can be administered by means of a suppository. A vehicle which has a melting point at about body temperature or one that is readily soluble can be utilized. For example, cocoa butter and various polyethylene glycols (Carbowaxes) can serve as the vehicle.

For intranasal instillation, a fluid unit dosage form is prepared utilizing an active ingredient and a suitable pharmaceutical vehicle, preferably pyrogen free ("P.E") water. A dry powder can be formulated when insufflation is the administration of choice.

For use as aerosols, the active ingredients can be packaged in a pressurized aerosol container together with a gaseous or liquefied propellant, for example, dichlorodifluoromethane, carbon dioxide, nitrogen, propane, and the like, with the usual adjuvants such a cosolvents and wetting agents, as may be necessary or desirable.

The term "unit dosage form" as used in the specification and claims refers to physically discrete units suitable as unitary dosages for human and animal subjects, each unit containing a predetermined quantity of active material calculated to produce the desired therapeutic effect in association with the required pharaceutical diluent, carrier or vehicle. The specifications for the novel unit dosage forms of this invention are dictated by and are directly dependent on (a) the unique characteristics of the active material and the particular therapeutic effect to be achieved, and (b) the limitation inherent in the art of compounding such an active material for therapeutic use in humans, as disclosed in this specification, these being features of the present invention. Examples of suitable unit dosage forms in accord with this invention are tablets, capsules, troches, suppositories, powderpackets, wafers, cachets, teaspoonfuls, tablespoonfuls, dropperfuls, ampules, vials, segregated multiples of any of the foregoing, and other forms as herein described.

The active ingredients to be employed as antineoplastic agents can be easily prepared in such unit dosage form with the employment of pharmaceutical materials which themselves are available in the art and can be prepared by established procedures. The following preparations are illustrative of the preparation of the unit dosage forms of the present invention, and not as a limitation thereof.

EXAMPLE 1

Several dosage forms were prepared embodying the present invention. They are shown in the following examples in which the notation "active ingredient" signifies dolastatin 14 its synthetic counterpart and the non-toxic pharmaceutically active derivatives thereof.

COMPOSITION "A"

Hard-Gelatin Capsules

One thousand two-piece hard gelatin capsules for oral use, each capsule containing 20 mg of an active ingredient are prepared from the following types and amounts of ingredients:

| | |
|---|---|
| Active ingredient, micronized | 20 gm |
| Corn Starch | 20 gm |
| Talc | 20 gm |
| Magnesium stearate | 2 gm |

The active ingredient, finely divided by means of an air micronizer, is added to the other finely powdered ingredients, mixed thoroughly and then encapsulated in the usual manner.

The foregoing capsules are useful for treating a neoplastic disease by the oral administration of one or two capsules one to four times a day.

COMPOSITION "B"

Tablets

One thousand tablets, each containing 20 mg of an active ingredient are prepared from the following types and amounts of ingredients.

| | |
|---|---|
| Active ingredient micronized | 20 gm |
| Lactose | 300 gm |
| Corn starch | 50 gm |
| Magnesium stearate | 4 gm |
| Light liquid petrolatum | 5 gm |

The active ingredient finely divided by means of an air micronizer, is added to the other ingredients and then thoroughly mixed and slugged. The slugs are broken down by forcing through a Number Sixteen screen. The resulting granules are then compressed into tablets, each tablet containing 20 mg of the active ingredient.

The foregoing tablets are useful for treating a neoplastic disease by the oral administration of one or two tablets one to four times a day.

Using the procedure above, tablets are similarly prepared containing an active ingredient in 25 gm and 10 gm of an active ingredient for the 20 gm used above.

COMPOSITION "C"

Oral Suspension

One thousand ml of an aqueous suspension for oral use, containing in each teaspoonful (5 ml)dose, 5 mg of an active ingredient, is prepared from the following types and amounts of ingredients:

| | |
|---|---|
| Active ingredient micronized | 1 gm |
| Citric acid | 2 gm |

-continued

| | |
|---|---|
| Benzoic acid | 1 gm |
| Sucrose | 790 gm |
| Tragacanth | 5 gm |
| Lemon Oil | 2 gm |
| Deionized water, q.s. 1000 ml | |

The citric acid, benzoic acid, sucrose, tragacanth and lemon oil are dispersed in sufficient water to make 850 ml of suspension. The active ingredient finely divided by means of an air micronizer, is stirred into the syrup until uniformly distributed. Sufficient water is added to make 1000 ml.

The composition so prepared is useful for treating a neoplastic disease at a dose of 1 tablespoonful (15 ml) three times a day.

COMPOSITION "D"

Parenteral Product

A sterile aqueous suspension for parenteral injection, containing in 1 ml, 30 mg of an active ingredient for treating a neoplastic disease, is prepared from the following types and amounts of ingredients:

| | |
|---|---|
| Active ingredient, micronized | 30 gm |
| Polysorbate 80 | 5 gm |
| Methyparaben | 2.5 gm |
| Propylparaben | 0.17 gm |
| Water for injection, q.s. 1000 ml | |

All the ingredients, except the active ingredient, are dissolved in the water and the solution sterilized by filtration. To the sterile solution is added the sterilized active micronizer, and the final suspension is filled into sterile vials and the vials sealed.

The compositon so prepared is useful for treating aneoplastic disease at a dose of 1 milliliter (1 M) three times a day.

COMPOSITON "E"

Suppository, Rectal and Vaginal

One thousand suppositories, each weighing 2.5 gm and containing 20 mg of an active ingredient are prepared from the following types and amounts of ingredients:

| | |
|---|---|
| Active ingredient, micronized | 1.5 gm |
| Propylene glycol | 150 gm |
| Polyethylene glycol #4000, q.s. | 1,500 gm |

The active ingredient is finely divided by means of an air micronizer and added to the propylene glycol and the mixture passed through a colloid mill until uniformly dispersed. The polyethylene glycol is melted and the propylene glycol dispersion added slowly with stirring. The suspension is poured into unchilled molds at 40° C. The composition is allowed to cool and solidify and then removed from the mold and each suppository is foil wrapped.

The foregoing suppositories are inserted rectally or vaginally for treating a neoplastic disease.

COMPOSITION "F"

Intranasal Suspension

One thousand ml of a sterile aqueous suspension for intranasal instillation is prepared, containing 20 mg of an active ingredient per ml of suspension, from the following types and amounts of ingredients:

| | |
|---|---|
| Active ingredient, micronized | 1.5 gm |
| Polysorbate 80 | 5 gm |
| Methylparaben | 2.5 gm |
| Propylparaben | 0.17 gm |

All the ingredients, except the active ingredient, are dissolved in the water and the solution sterilized by filtration. To the sterile solution is added the sterilized active ingredient, finely divided by means of an air micronizer, and the final suspension is aseptically filled into sterile containers.

The composition so prepared is useful for treating a neoplastic disease, by intranasal instillation of 0.2 to 0.5 ml given one to four times a day.

An active ingredient can also be present in the undiluted pure form for use locally about the cutis, intranasally, pharyngolaryngeally, bronchially, or orally.

COMPOSITION "G"

Powder

Five grams of an active ingredient in bulk form is finely divided by means of an air micronizer. The micronized powder is placed in a shaker-type container.

The foregoing composition is useful for treating a neoplastic disease, at localized sites by applying a powder one to four times per day.

COMPOSITION "H"

Oral Powder

Ten grams of an active ingredient in bulk form is finely divided by means of an air micronizer. The micronized powder is divided into individual doses of 20 mg and packaged.

The foregoing powders are useful for treating a neoplastic disease, by the oral administration of one or two powders suspended in a glass of water, one to four times per day.

COMPOSITION "I"

Insufflation

Ten grams of an active ingredient in bulk form is finely divided by means of an air micronizer.

The foregoing compositon is useful for treating a neoplastic disease, by the inhalation of 30 mg one to four times per day.

COMPOSITION "J"

Hard Gelatin Capsules

One hundred two-piece hard gelatin capsules for oral use, each capsule containing 20 mg of an active ingredient.

The active ingredient is finely divided by means of an air micronizer and encapsulated in the usual manner.

The foregoing capsules are useful for treating a neoplastic disease, by the oral administration of one or two capsules, one to four times a day.

Using the procedure above, capsules are similarly prepared containing active ingredient in 5, 25, and 50 mg amounts by substituting 5 gm, 25 gm and 50 gm of the active ingredient for the 20 gm used above.

EXAMPLE 2

Unit dosage forms of dolastatin 14, prepared according to selected compositions described in Example 1, were screened utilizing Protocol 1,200 described in *Cancer Chemotherapy Reports, part* 3, Vol. 3, No. 2, September 1972, pp 9 et seq for lymphocytic leukemia P388 Dolastatin 14 markedly inhibited growth of the P388 in vitro cell line ($ED_{50}=2.4\times10^{-3}$ μg/ml).

From the foregoing it becomes readily apparent that a new and useful cell growth inhibitory factor and new and useful antineoplastic preparations have been herein described and illustrated which fulfill all of the aforestated objectives in a remarkedly unexpected fashion. It is of course understood that such modifications, alterations and adaptations as will readily occur to the artisan confronted with this disclosure are intended within the spirit of the invention which is limited only by the scope of the claims appended hereto.

Accordingly, what is claimed is:

1. An isolated cell growth inhibitory substance denominated dolastatin 14 and having the structural formula:

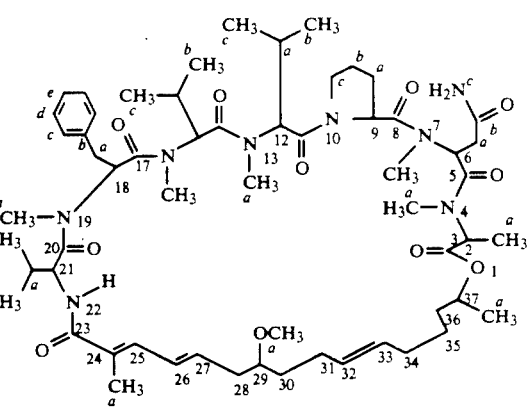

2. A substance according to claim 1 which is pure.

* * * * *